US008575525B2

(12) United States Patent
Mackay et al.

(10) Patent No.: US 8,575,525 B2
(45) **Date of Patent: *Nov. 5, 2013**

(54) TUNNEL FOR CONDITIONING OF PRODUCTS, ESPECIALLY FOR STERILIZATION OF FOOD IN PREPACKAGED CONTAINERS

(76) Inventors: Jeffrey H. Mackay, San Diego, CA (US); Renato Giordano, San Juan Capistrano, CA (US); Randall J. Lanham, Rancho Santa Margarita, CA (US); Rod Corder, Chesterton, IN (US)

( * ) Notice: Subject to any disclaimer, the term of this patent is extended or adjusted under 35 U.S.C. 154(b) by 1190 days.

This patent is subject to a terminal disclaimer.

(21) Appl. No.: 11/883,740

(22) PCT Filed: Dec. 23, 2005

(86) PCT No.: PCT/US2005/046925

§ 371 (c)(1), (2), (4) Date: Jun. 22, 2009

(87) PCT Pub. No.: WO2006/073909

PCT Pub. Date: Jul. 13, 2006

(65) Prior Publication Data

US 2009/0283517 A1 Nov. 19, 2009

(51) Int. Cl.

| | |
|---|---|
| ***H05B 6/78*** | (2006.01) |
| ***H05B 6/66*** | (2006.01) |
| ***C11B 1/04*** | (2006.01) |
| ***A61L 2/24*** | (2006.01) |
| ***A23C 3/07*** | (2006.01) |
| ***A23L 3/00*** | (2006.01) |
| ***A23L 1/164*** | (2006.01) |
| ***A01J 11/04*** | (2006.01) |
| ***A01J 13/00*** | (2006.01) |
| ***A01J 15/14*** | (2006.01) |
| ***A23C 3/02*** | (2006.01) |
| ***A23C 15/04*** | (2006.01) |
| ***B65B 55/00*** | (2006.01) |

(52) U.S. Cl.
USPC ........... 219/700; 219/701; 219/702; 422/308; 422/3; 99/451; 99/467; 99/483; 426/234; 426/241

(58) Field of Classification Search
USPC ............ 422/308, 21, 483, 304; 219/698, 728, 219/745, 748, 697, 700–702; 99/451, 483, 99/477, 417, DIG. 14; 426/234, 465, 426/241–243
See application file for complete search history.

(56) References Cited

U.S. PATENT DOCUMENTS 3,138,239 A 6/1964 Ackerman et al.

(Continued)

*Primary Examiner* — Quang Van
*Assistant Examiner* — Michael Hoang
(74) *Attorney, Agent, or Firm* — Russo & Duckworth, LLP; David G. Duckworth

(57) ABSTRACT

Tunnel is provided for conditioning of food products, especially for sterilization of food in containers or vessels of the heat-sealed type, in which the conditioning unit has: 1) an active temperature and pressure control system provided in at least one magnetron supported heating stage, which provides for balancing of the pressure within the heat-sealed vessels or containers; 2) a conveyor which conveys the heat-sealed vessels or containers through the stages along the conditioning unit which contains mechanisms that move the conveyor outside of the conditioning tunnel, and 3) doors operating like check valves that separate the conditioning stages, but still provide for continuous linear feed of products through conditioning tunnel. Movement of the magnetron electromagnetic field and/or conveyor is controlled by software which utilizes the temperature and/or density measurements in a closed loop process to ensure uniform heating of the products.

2 Claims, 12 Drawing Sheets

(56) References Cited

U.S. PATENT DOCUMENTS

| | | | | |
|---|---|---|---|---|
| 3,506,825 | A * | 4/1970 | Hartmann | 378/69 |
| 3,889,009 | A * | 6/1975 | Lipoma | 426/234 |
| 5,132,504 | A | 7/1992 | Iijima | |
| 6,039,991 | A * | 3/2000 | Ruozi | 426/241 |
| 6,294,773 | B1 * | 9/2001 | Chung | 219/701 |
| 6,413,481 | B1 * | 7/2002 | Pennekamp et al. | 422/302 |
| 6,499,274 | B1 | 12/2002 | McDonald et al. | |
| 6,690,020 | B2 * | 2/2004 | Loda | 250/455.11 |
| 7,361,303 | B2 * | 4/2008 | Kantor et al. | 422/22 |
| 7,993,603 | B2 * | 8/2011 | Amedeo et al. | 422/308 |
| 2002/0010502 | A1 * | 1/2002 | Trachtenberg | 607/102 |
| 2003/0121914 | A1 * | 7/2003 | Linn et al. | 219/745 |
| 2004/0131519 | A1 * | 7/2004 | Amedeo et al. | 422/308 |
| 2006/0231550 | A1 | 10/2006 | Wendel et al. | |

* cited by examiner

TUNNEL FOR CONDITIONING OF PRODUCTS, ESPECIALLY FOR STERILIZATION OF FOOD IN PREPACKAGED CONTAINERS

BACKGROUND OF THE INVENTION

The present invention relates to methods and apparatus for sanitizing items. More particularly, the invention relates to improved microwave cooking systems having a plurality of linearly aligned segments for processing food products.

The invention finds special, but not exclusive application in the sector of collective catering, where sterilization treatment of foods already sealed in containers not to be consumed immediately is required. A second possible application can also concern sterilization or sanitization of other products intended for the food chain, like flour, rice, as well as specific products of various nature, prepared or not, and medicinal products or parts of them. Still a third application of the present invention concerns the sterilization of medical equipment.

Techniques for conditioning foods for serving of meals to a large number of persons, for example, are certainly known, as occurs in dining halls, in hospitals and other facilities, where large numbers of persons make traditional catering untenable, at least in terms of cost. On the practical side, these techniques can be summarized in three basic steps: a) selection and precooking of foods; b) preservation; and c) serving.

Conventionally, a cycle of selection and precooking of foods is followed by a preservation cycle, which typically includes the use of refrigerators or freezers and, in more recent techniques, rapid heating vessels.

In some cases, where preservation on an industrial scale is required, a post-preparation sterilization phase is required between the first and second stages, which, as in the case of use of a container alone, is not limited to attenuation of microbial, pathogenic and enzymatic activity, but has the purpose of destroying all microorganisms present in the product, and also in the actual container/package. This occurs, because the degree of resistance to heat of microorganisms is related to external and environmental factors, like the initial microbial concentration of the medium, the characteristics of the medium itself and the time and temperature parameters, as well as intrinsic factors related to heat sensitivity of germs, development stage of the cells, in which specific variations often occur. For example, under identical environmental conditions, it is observed that fungi and yeast are more resistant than coli bacteria and, within the latter, the rod forms are more resistant that the coccal forms.

Under practical conditions, to carry out sterilization, it is necessary to heat the product to a temperature between 65° C. and 121° C. for a time of between 5 and 12 minutes. Subsequently, the product must be subjected to the most rapid possible cooling to a temperature equal to or less than 35°.

The use of high frequency electromagnetic waves, in the form of microwaves, is known for performing the sterilization stage. In this sense, GB1103597 (Newton et al.) already suggested a system for controlling microorganisms contains in prepared foods and beverages. It prescribes for exposure of the already prepared foods with the package to electromagnetic waves with a frequency of 20-40 MHz at an intensity of 500-3000 volts for a sufficient period of time to attenuate the microorganisms present in the manufactured product. The use of microwave generators, referred to herein as magnetrons, to sterilize materials is known in even greater detail. For example, WO0102023 (Korchagin) proposes a magnetron that has the capacity to implement the intensity of the magnetic field at a level to ensure destruction of microorganisms.

Complex apparatuses, specifically continuous treatment tunnels for sanitization of packaged products, have been known since 1973. U.S. Pat. No. 3,747,296 (Zausner) proposes an apparatus with linear development, in which filled containers are introduced and subsequently closed. Said containers are passed through the tunnel, which is subdivided into different treatment zones at temperatures between 90° C. and 150° C. Means of irradiation are also provided, which have the purpose of sterilizing the cover only.

U.S. Pat. Nos. 5,066,503; 5,074,200; 5,919,506 and 6,039,991 issued to Ruozi describe conveyor driven microwave processing plants for pasteurizing, cooking and sterilizing food products. The plants include a plurality of chambers wherein the temperature and pressure are controllable elevated and decreased within as the food products travel from chamber to chamber.

U.S. Pat. No. 3,889,009 (Lipoma) describes a conditioning tunnel for foods previously prepared in bowls and sealed under pressure. The conditioning tunnel essentially consists of an external covering, along which a conveyor belt moves. At the entry and exit of this tunnel, corresponding to the crossing point of the manufactured vessels, pressure closure doors are provided. Once the sealed vessels have entered the interior of the tunnel, each vessel undergoes a sterilization treatment, passing beneath a source of electromagnetic waves. Each vessel is then transferred downline, always by means of a common belt or chain conveyor, to pass through a cooling unit. A device to generate pressure during the sterilization phase operates within the apparatus to avoid a situation in which the products, because of the process, burst because of the dilation effect, or whose sealing strength is altered. This phenomenon most frequently entails escape of liquid from individual containers, producing not insignificant drawbacks within the apparatus, like accumulation of dirt and the subsequent need to carry out frequent maintenance.

Other apparatuses based on developments of the system just described are also known. For example, in the catalogs of the Italian companies Modo Group International from Brescia Italy and Micromac from Reggio Emilia, automatic and computerized tunnels are described, which provide for receiving the products, in this case prepared dishes in a heat-sealed vessel, and are designed to carry out the fundamental phases of sterilization treatment. The tunnels include elongate cylindrical constructions have diametrically round cross sections, within which, corresponding to the different stages, the following process phases are conducted: 1) preheating; 2) reaching the sterilization temperature by means of induction devices that generate microwaves; 3) holding or stabilization of the product at the sterilization temperature for a specified time (magnetrons, which are positioned along the lower side of the conditioning tunnel beneath or corresponding to the plane of advance of the prepared foods, are typically provided to execute at least these last two phases); and 4) cooling before unloading. At the end of the process, a finished product emerges, completely sanitized and ready to be packaged and stored in warehouses.

Unfortunately, the prior art food processing systems suffer from numerous disadvantages. In particular, the previous solutions provide for the necessary magnetrons for gradual reaching and maintenance of the temperature within each product. These devices are situated indifferently along the overlying or underlying side of the line of advance of the heat-sealed bowls/trays/vessels.

Further problems are associated with the characteristics of the non-return valves that divide each of the stages present along the tunnels of the traditional type. These valves are of the mechanical opening and closing type, whereas the movement that they execute is essentially along a linear axis, using fittings situated peripherally to the closure plate. The negative aspect of these solutions concerns the fact that they are fairly complex and require accurate and constant maintenance to ensure, between the different treatment stages, maintenance of the pressure present in the concerned section.

SUMMARY OF THE INVENTION

These and other purposes are accomplished with the present innovation by providing a conditioning tunnel for products, especially for sterilization of food in trays or bowls of the heat-sealed type, including a conditioning unit of the food products, consisting of a tunnel, in which a controlled pressure prevails, subdivided into stages, each stage corresponding to a phase of the treatment cycle that includes at least one heating phase and a cooling phase; a conveyor of the food products from upline to downline through the conditioning unit; pressure sealing doors arranged along the conditioning unit that separate each stage from the adjacent stage; and means of heating at least one stage of the conditioning unit containing a series of magnetrons. The conditioning unit has an active pressure control system corresponding to at least one heating stage, in which pressure equalization within the heat-sealed trays or bowls is prescribed; a conveyor level, which, through the stages, conveys the heat-sealed trays or bowls along the conditioning unit, which contains mechanisms that can be moved in the plane of the conveyor, positioned outside of the conditioning tunnel; check valves that separate the stages of the conditioning unit; and a cross section of the tunnel of the polygonal type; and corresponding to at least one stage of the conditioning unit, a washing liquid input header with corresponding unloading; as well as devices for protection from liquids of each magnetron.

The heating stage includes numerous improvements over previous designs. The heating stage include pressure sealing doors, also referred to as check valves, which provide a substantial air tight chamber for cooking products. The pressure sealing doors may be constructed to include an openable and closeable gate valve. Alternatively, the pressure sealing doors may be constructed as a rotating drum positioned in a sealing arrangement with the entrance and exit of the one or more heating stages. The rotating drum includes one or more recesses for receipt of products to be introduced into the heating stages. Rotation of the drum is continuous to permit the continuous introduction and discharge of products into and from the heating stages without having to continuously pressurize and depressurize the heating chamber with each introduction of products.

Advantageously, the heating stages include a plurality of magnetrons for conditioning products. The magnetrons are preferably positioned at right angles to the products being treated, such as positioned directly above, below and/or to the sides of the products as they are conveyed through the tunnel. In a preferred embodiment, magnetrons produce electromagnetic energy at two or more distinct frequency bands, in order to cook product at different depths. Preferably, the magnetrons include at least one magnetron producing electromagnetic energy at greater than about 2000 Mhz and at least one magnetron producing electromagnetic energy at less than about 1000 Mhz. Even more preferably, the magnetrons produce electromagnetic energy at distinct frequency bands at approximately 915 Mhz and 2450 Mhz.

Preferably, the conditioning unit includes one or more temperature sensors for measuring and recording the temperature of products traveling through the conditioning tunnel. The temperature sensors may take various forms. In a preferred embodiment, the temperature sensors are pyrometers, such as laser pyrometers, capable of providing two dimensional mapping of the surface temperatures of products passing through the conditioning tunnel. Even more preferably, the conditioning unit includes at least two pyrometers for temperature mapping two or more surfaces, such as the top and bottom, of products within the conditioning tunnel. Preferably, the plurality of two dimensional temperature maps are processed by a computer processor to develop three dimensional temperature distribution maps of products traveling through tunnel.

Preferably, the conditioning unit includes a control unit for processing temperature measurements and/or temperature distribution maps for adjusting the electromagnetic field as encountered by products within the conditioning tunnel. The electromagnetic field may be adjusted by several methods including: altering the power output of the magnetrons, by physically moving the magnetrons, or by altering the position or movement of the products within the conditioning tunnel, such as by causing the conveyor to move the products upline or downline relative to the magnetrons.

The conditioning tunnel includes an automated conveyor system for moving products. Preferably, conveyor system includes mechanisms for advancing products primarily exterior to the tunnel for making the conditioning unit more reliable in terms of the profile of components, significantly reducing maintenance, and reducing the down times of the machine. The exterior conveyor system also significantly increases the useful treatment capacity of the conditioning tunnel, and also has the purpose of reducing formation of receptacles and spaces, where dirt can accumulate, and the development of bacterial colonies that are difficult to remove because of their location.

The present invention optimizes the conditioning cycle of the food products, which comprises the phases of sterilization. This objective is essentially made possible by the presence of distinct and consecutive phases conducted in the respective stages of a conditioning unit, specifically preheating, heating and stabilization (or holding at a temperature for a certain period of time), each phase prescribing a controlled pressure within the respective stage that balances the pressure relative to the interior of the individual product.

These and other advantageous or purposes will be apparent from the subsequent detailed description of some preferred solutions of the implementation by means of the appended schematic drawings, whose details are not intended to limit the invention, but merely exemplify it.

DETAILED DESCRIPTION OF THE INVENTION

Figure 1:
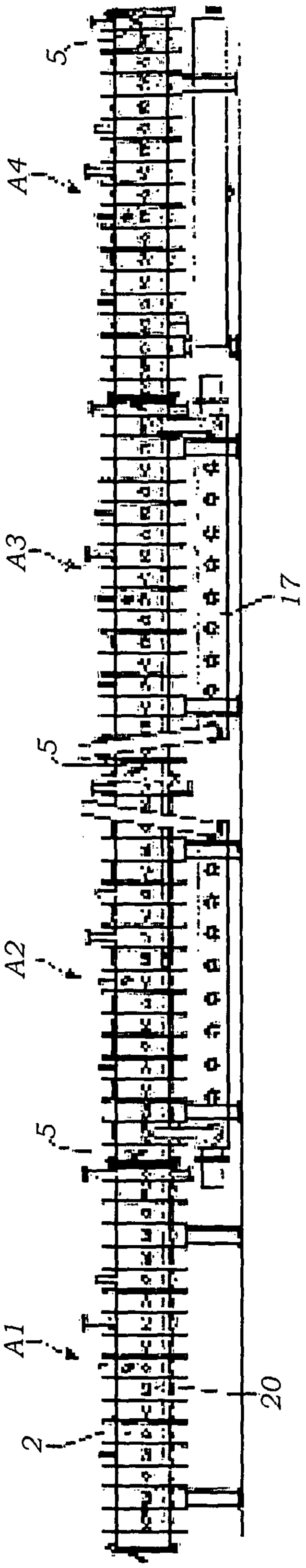
FIG. 1 is a side view of the conditioning unit, especially for food products, that provides four distinct stages, connected in succession.
Figure 2:
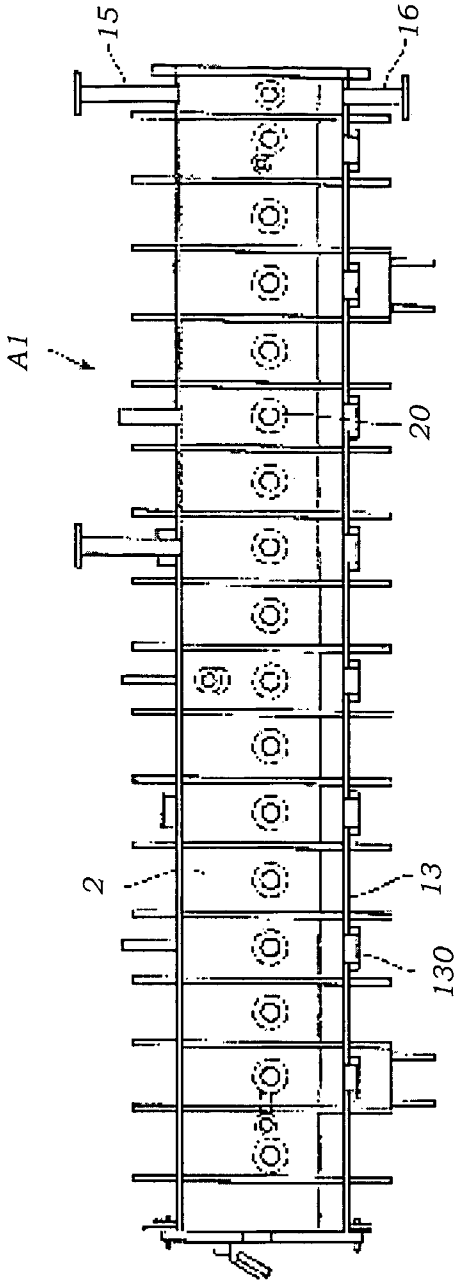
FIG. 2 is a side view of the first preheating stage, provided along the conditioning unit according to FIG. 1.
Figure 3:
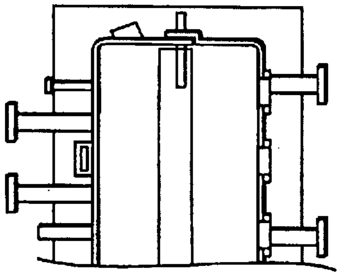
FIG. 3 is a cross sectional view of the first stage of the conditioning tunnel according to FIG. 2.
Figure 4:
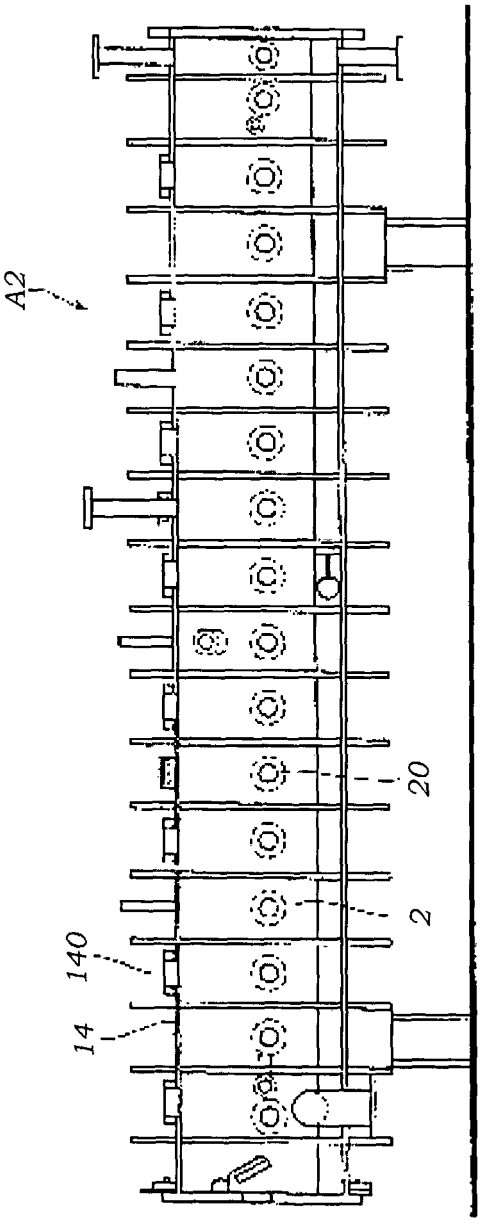
FIG. 4 is a side view of the second heating stage of the conditioning unit of FIG. 1.
Figure 5:
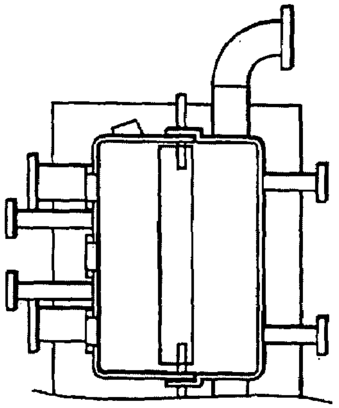
FIG. 5 is a cross sectional view of the second stage of the conditioning tunnel according to FIG. 4.
Figure 6:
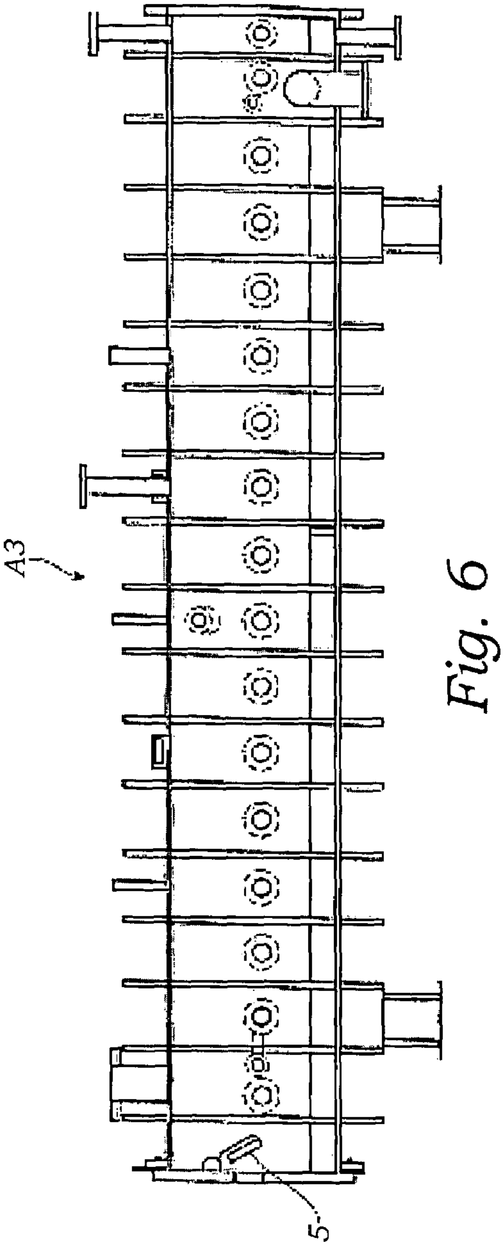
FIG. 6 is a side view of the third stage, corresponding to stabilization or temperature holding in the conditioning tunnel according to FIG. 1.
Figure 8:
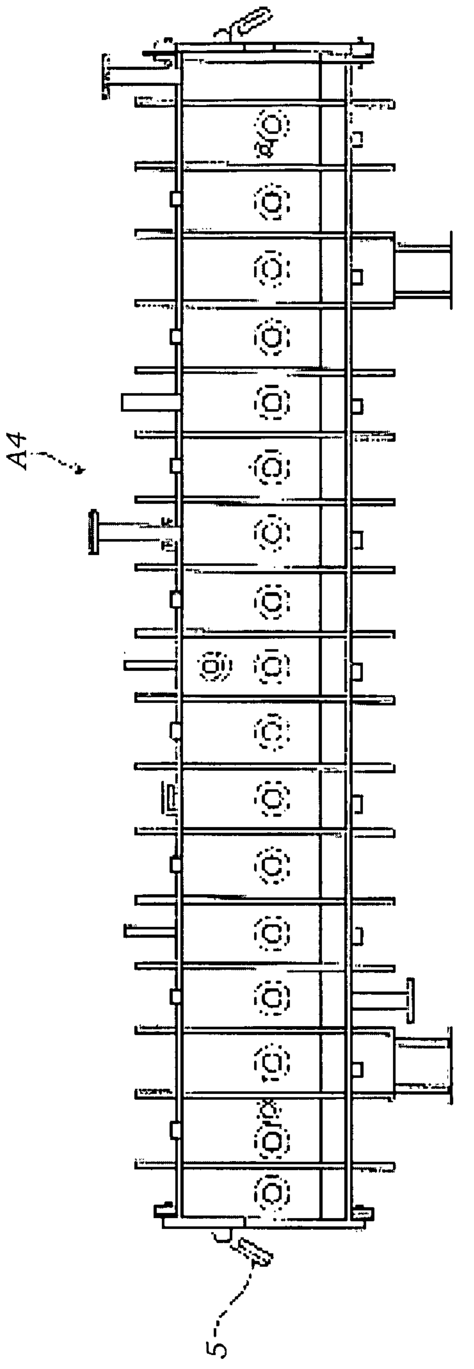
FIG. 8 is a side view of the fourth stage, where the cooling phase develops in the conditioning tunnel according to FIG. 1.
Figure 9:
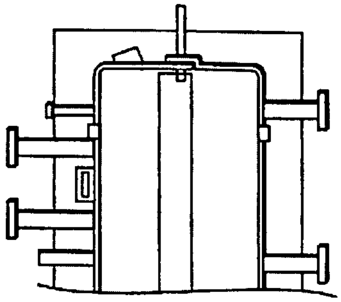
FIG. 9 is a cross sectional view of the fourth stage of the conditioning tunnel according to FIG. 1.
Figure 7:
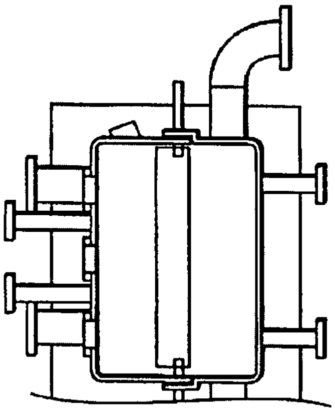
FIG. 7 is a cross section of the fourth stage in the conditioning tunnel according to FIG. 1.
Figure 10:
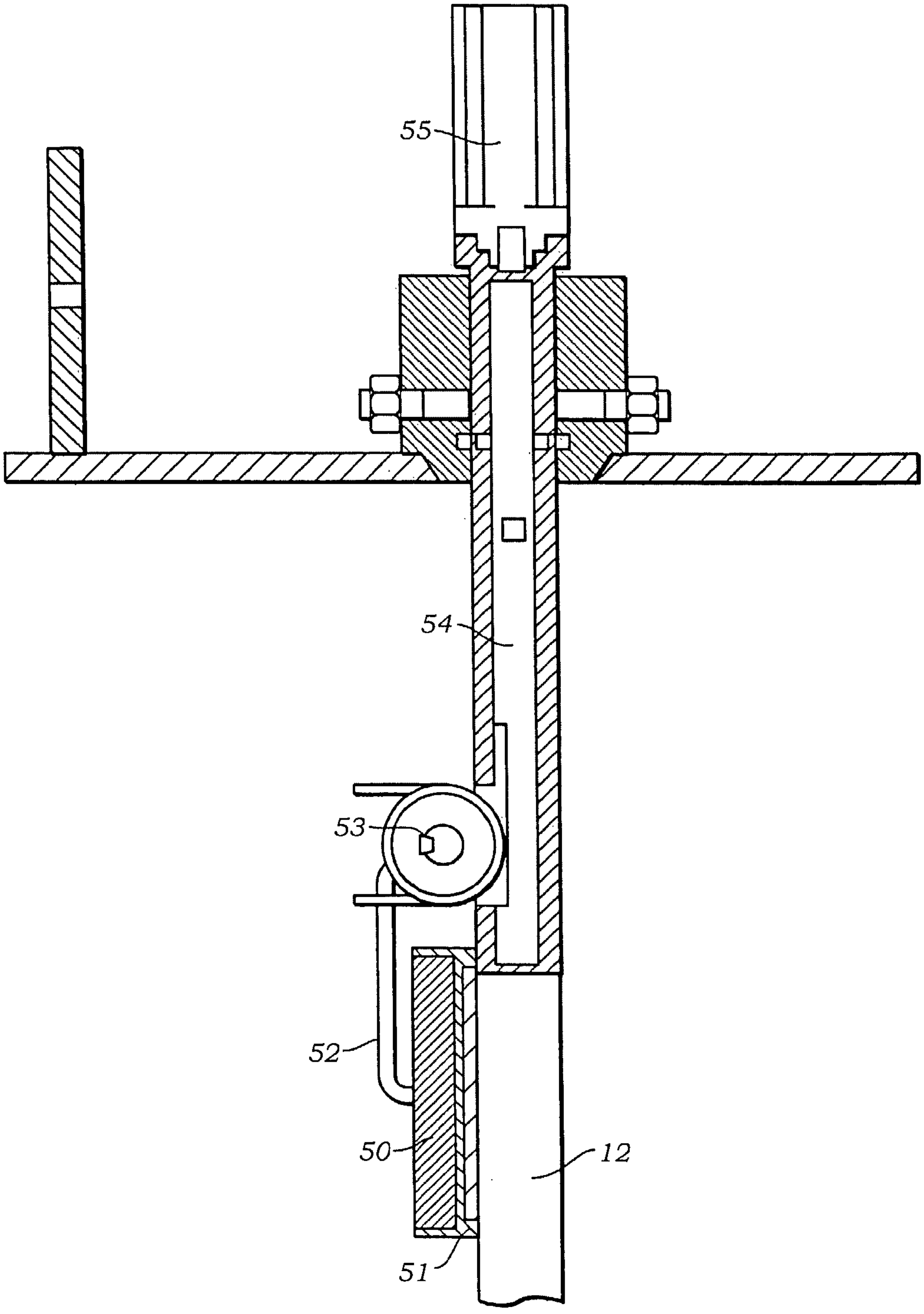
FIG. 10 is a cross-sectional view of the zone affected by the check valve, which connects two adjacent stages in the conditioning tunnel according to FIG. 1.
Figure 11:
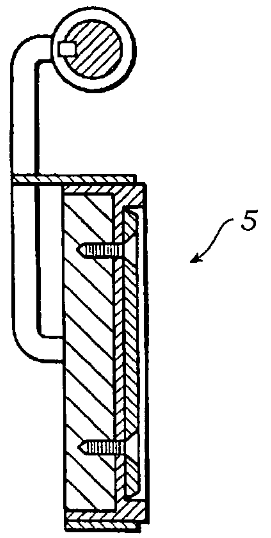
FIG. 11 is a cross-sectional view of a single check valve door.

With reference to the Figures, a conditioning tunnel A is provided for the sterilization and sanitation or various products including medical equipment, food products and other items. Because the conditioning tunnel A is believed to have particular application for the sterilization, sanitization and cooking of foods already packaged in heat-sealed plates, bowls or trays 1, the conditioning tunnel of the present invention is described with particular application to the processing of food products. However, the conditioning tunnel is not limited thereto, and may be used to process innumerable other items.

As shown in the figures, the conditioning tunnel may include any number of segments A1-A4 for treating the food products. The food conditioning process includes two primary stages: a microwave sterilization process and a cooling down process. In addition, the food conditioning process may include a third stage referred to herein as an initial temperature stabilization process which may, or may not, be conducted within the automated conditioning tunnel of the present invention.

The initial temperature stabilization process ensures product uniformity during the microwave sterilization and cooling down processes. The ability to properly sterilize the food product ultimately depends on the uniform heating of the product before it reaches the final temperature treatment in the convection heating chamber. This, in turn requires the product uniformity for the input stages of both the top-side irradiation and the bottom-side irradiation phases. Product uniformity consists of both mass and temperature uniformity. Product mass uniformity is ensured by weighing the product before entry into the sterilization system and rejecting products outside the bounds of the product recipe. In addition, the distribution of the food product must be uniform inside the packaging, and can be assured by mechanical means such as vibration settling. Since the prepared product may be composed of several different components at differing temperatures (not only different initial temperatures, but the temperature of components may fluctuate during the packaging phase), care must be taken to ensure that, before entering the microwave irradiation chamber, the product temperature is as uniform and predictable as possible. It is important to note that the permitivity (å') and dielectric loss factor (å") of foods change with temperature. Since the rate of heating as well as the characteristic impedance under microwave irradiation is directly proportionate to both the permitivity (å') and the dielectric loss factor (å"), it is important that those parameters be uniform in the product as well.

Initial temperature stabilization and uniformity is a two-step process. First, the incoming product temperature is measured. If this temperature is below a recipe minimum, the product may be rejected, or subjected to further temperature stabilization before processing. Second, the product temperature is brought up to a uniform temperature, preferably above ambient temperature to allow the temperature of all of the product components to stabilize. This second stage is typically done in a convection oven or conduction hot-plate, and held for a time. The holding time may be derived empirically, or by using the thermal impedances and masses of the product components. This holding time must be sufficient to ensure that the coolest components are given time to heat up by conduction within the product container. For a food product that does not have significant liquids for heat conduction, such as grains or rice, it is important that the temperature stabilization time be adequate to ensure uniform heat conduction across and through the product.

Figure 15:
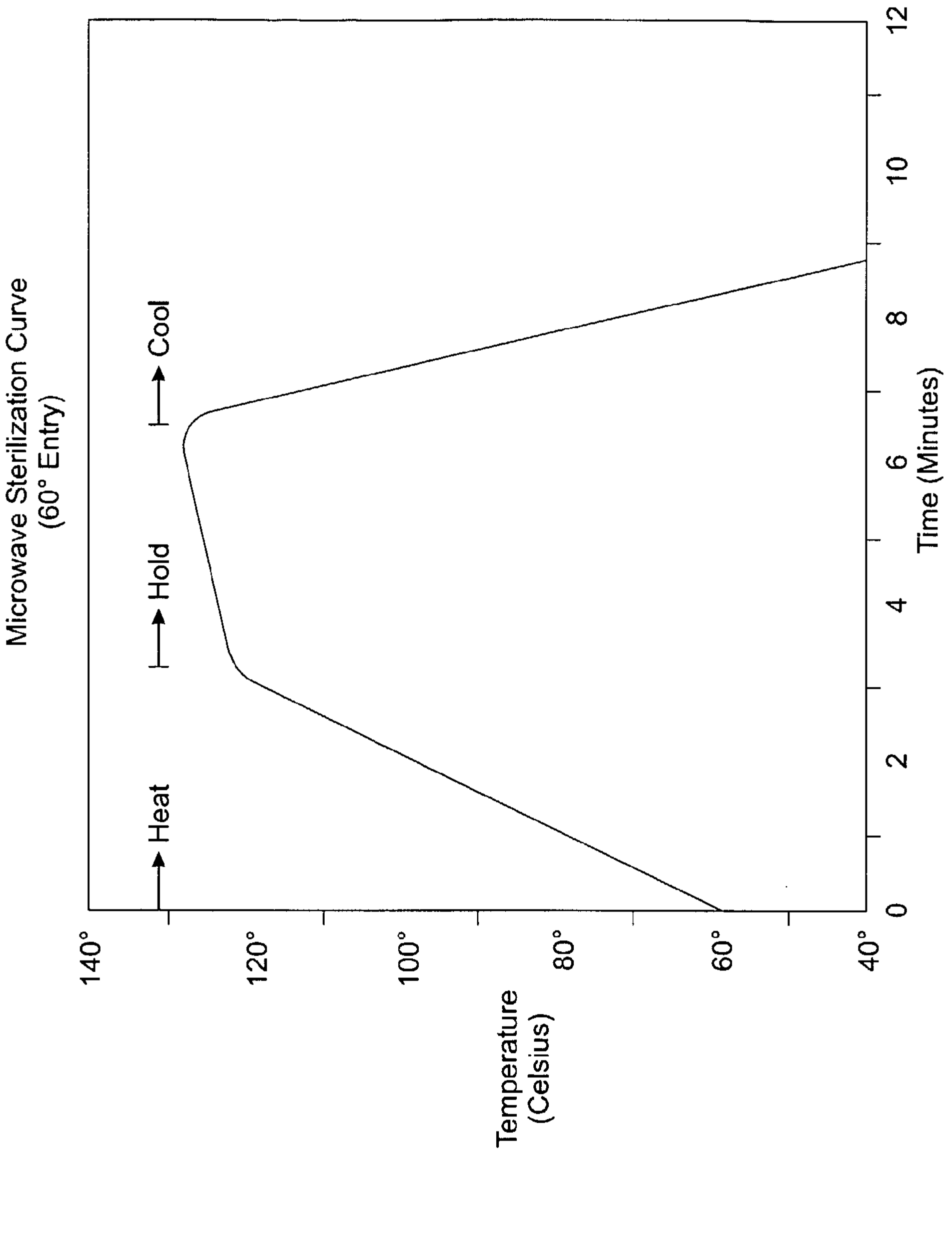
FIG. 15 is a first preferred graph illustrating the cooking parameters of temperature and time provided by a food processing system of the present invention.
Figure 16:
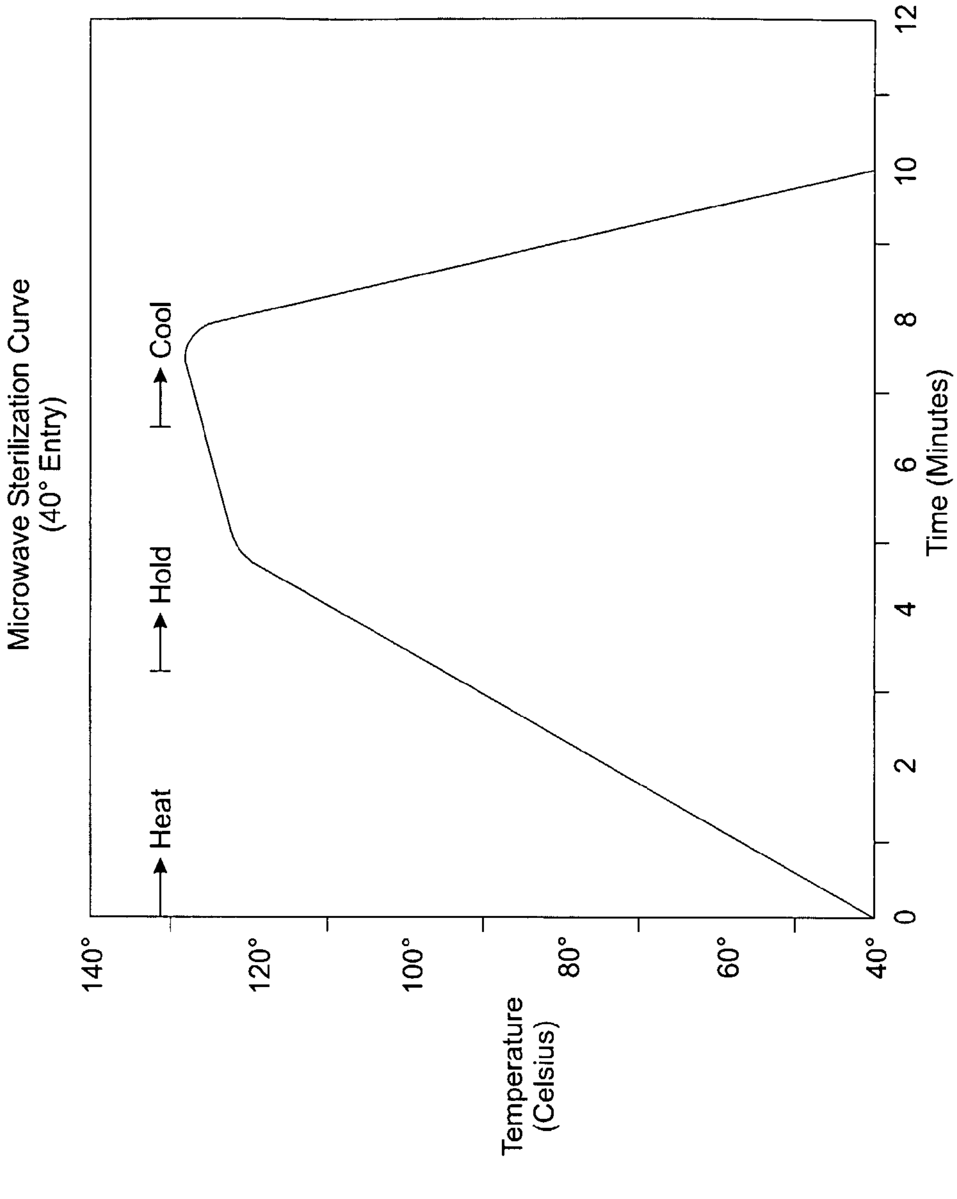
FIG. 16 is a second preferred graph illustrating the cooking parameters of temperature and time provided by a food processing system of the present invention.

With reference to FIGS. 15 and 16, the microwave sterilization process takes place in a pressurized chamber from top and bottom electromagnetic activity from magnetrons and temperature driven energy bursts to isolate and eliminate the possibility of "cold spots". Pressure is applied accordingly to prevent the sealed packages from exploding under the cooking temperature. At the end of cooking time, the chamber is depressurized and the food product is carried to a fast action thermal quench chamber to rapidly reduce the food temperature to ambient temperature. The cooling process can be achieved either by chilled water circulation or by a cryogenic controlled nitrogen environment.

To provide initial temperature stabilization, microwave sterilization processing, and cooling down processing, the conditioning tunnel A is provided which may include any number of segments. As shown in FIGS. 1-10, in a first preferred embodiment, the conditioning includes four segments A1-A4 to provide essentially linear development, through which the prepackaged products 1 transit longitudinally. The conditioning tunnel A is constructed by joining the head of one stage to the next one of the other three stages as preassembled modules, respectively, A1, A2, A3 and A4. Each of the four stages A1, A2, A3 and A4 represents a section of the conditioning tunnel A, within which one phase of the conditioning cycle is reproduced.

Figure 13:
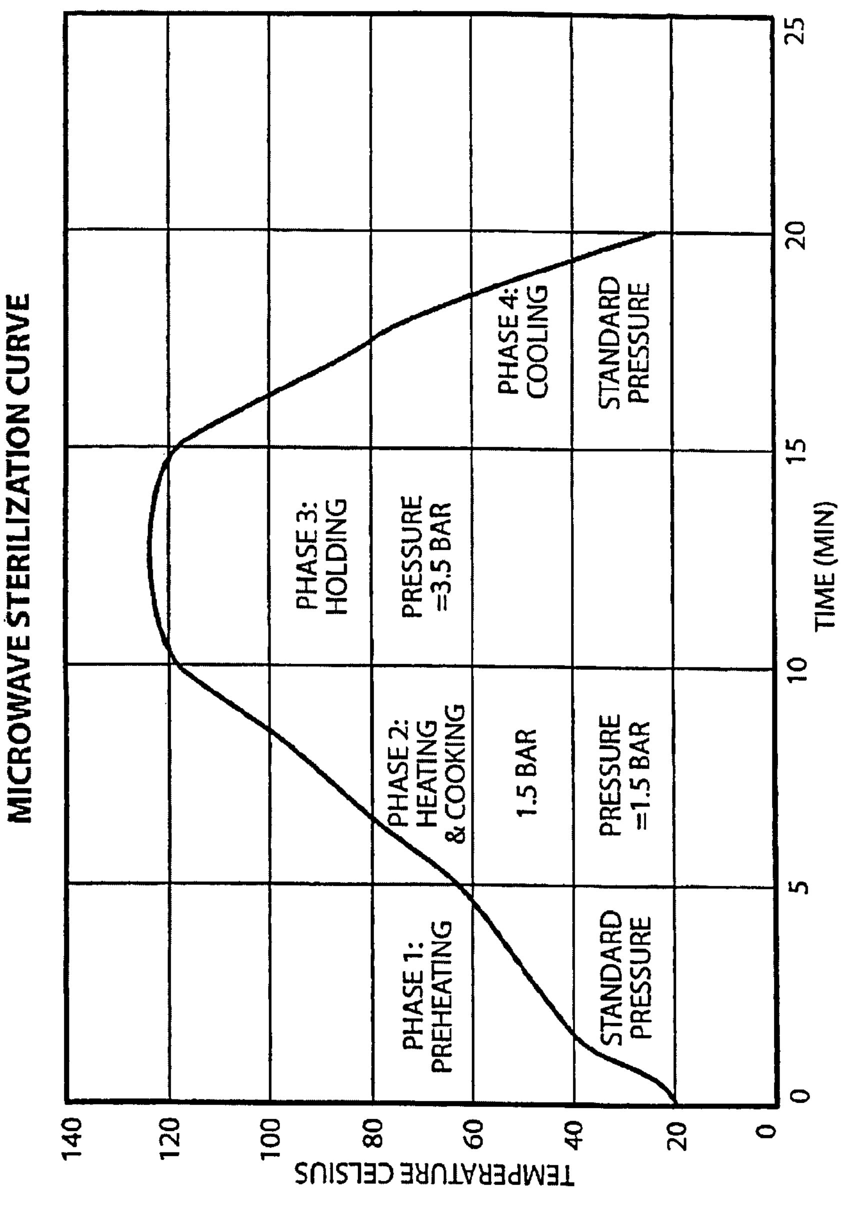
FIG. 13 is a graph illustrating the cooking parameters of temperature, pressure and time provided by a food processing system of the present invention.

The conditioning cycle may be conducted in innumerable ways, only one of which is described in detail. With reference to FIG. 13, a preferred conditioning cycle includes the stages of: A1) preheating; A2) heating and cooking; A3) holding; and A4) cooling. Along stage A1, the food, already packaged in plates, bowls or trays 1 and heat-sealed, is subjected to a first preheating phase that brings the dishes from an ambient temperature close to 20° C. to 50° C. Along the second stage A2, the packaged dishes coming from the upline phase are then brought from a temperature of about 50° C. to a temperature of about 120° C. The products 1 then enter a downline phase A3, along which the packaged dishes are held or stabilized for a specified period of time at a temperature no lower than 120° C. At the end of these three phases A1, A2 and A3, the packaged dishes are finally transferred downline along stage A4, within which a cooling phase is carried out.

Each stage A1, A2, A3 and A4 of tunnel A is characterized by a typical section that may have a circular or rectangular cross-section and coaxially has an interior chamber 11, also circular or rectangular in shape, that extends in width between the inside walls of the main chamber. The conditioning stages A1, A2 and A3 also may, or may not, include inlets permitting entry of supply of hot air and aspiration 17. Air supplied at approximately 130° Celsius is believed acceptable for processing and cooking most foods. Finally, preferably stage A4 includes a cooling system including inlets, or nozzles, projecting through the stage A4 sidewalls for presentation of a cold water spray for cooling the food products. The water preferably includes an anti-freeze additive, as can be selected by those skilled in the art, for ensuring that the cooling spray is supplied at about 1° Celsius and does not freeze and clog the water inlets.

Any, or all, of the stages A1-4 may include additional cleaning fluid inlets for washing the interior of the conditioning tunnel. To this end, the stages may include nozzles projecting through the stages' sidewall which are connected to a supply of cleaning fluid. to permit washing of the interior of the stages. To this end, water inlets 15 and corresponding discharges 16 are provided, positioned along each stage.

Figure 12:
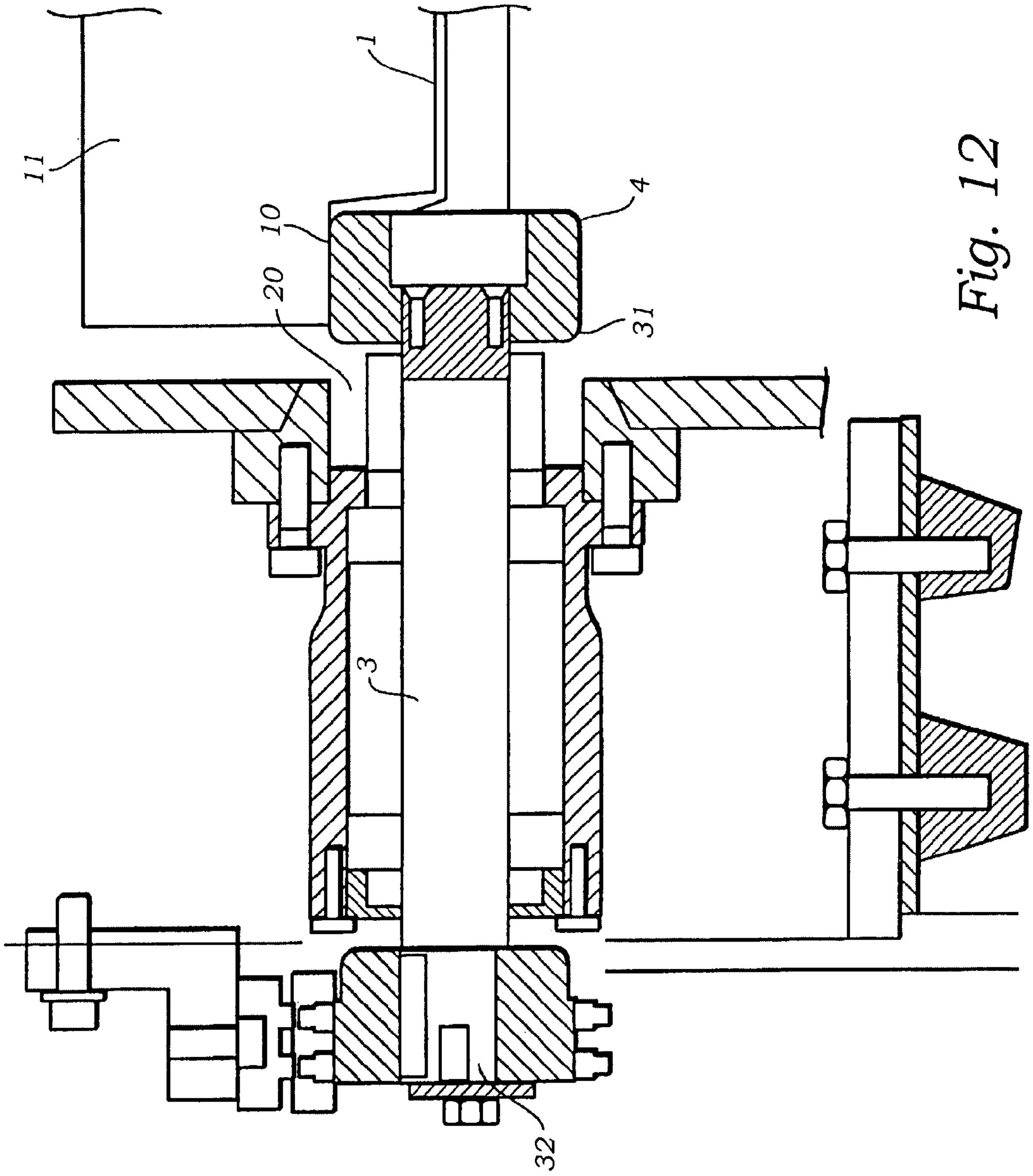
FIG. 12 is a cross sectional view of the conveyor of the heat-sealed vessels.

As shown in FIG. 12, in a preferred embodiment of the invention, the means for conveying the products through the conditioning tunnel is preferably located outside of the tunnel. To this end, along the flanks of the linear structure of each stage A1, A2, A3 and A4, apertures 20 are provided. The apertures 20 are longitudinally aligned and equidistantly positioned through the sidewalls of the chamber 11. A support shafts 3 projects through the apertures from the outside of the conditioning tunnel, entering the inside 31 of the chambers 11 of stages A1, A2, A3 and A4. At the corresponding end 31 inside the chamber 11 of stage A1, A2, A3 and A4, a wheel 4 is mounted, which has the purpose of keeping the packaged dishes 1 in movement. As shown in FIG. 12, the wheels support and propel the food products 1, a shown bowls, which have, at least on the side, a protruding lip 10 that is supported on the wheel 4. Rotation of one or more of the wheels 4 along the left and right sides of stage A1, A2, A3 and A4 is caused one or more motors and chains drives. These means of transmission and rotary motion are positioned on the outside along each flank of the stages A1, A2, A3 and A4, engaging the end of shaft 3, which has on the opposite end a corresponding toothed wheel 32. In this manner, by interaction of wheels 4, an idler is obtained that moves longitudinally, from upline to downline, the packaged dishes 1 through each stage A1, A2, A3 and A4, in a logical sequence controlled by a logic control unit. Preferably, the conveyor can move the food products forward or rearward through the conditioning tunnel. Moreover, the conveyor may provide an oscillating movement of the food products forwardly, or forwardly and rearwardly, to alter the magnetic field seen by the packages to provide more uniform heating. For example, the conveyor may move food products forwardly, followed by periodic pauses, to provide uniform heating. Alternatively, the conveyor may move the products forwardly and rearwardly in an oscillating manner to provide uniform heating.

Advantageously, by providing the motors and chain, or other drive mechanism, exterior to the chamber, the conveyor provides a minimum of surfaces within the chambers which are capable of collecting dirt or accidentally spilled food products. Moreover, though the drive mechanism of the present invention may include a shaft which projects across the interior of the chambers 11, preferably, and as shown in FIG. 12, the drive mechanism includes wheels which project only a few inches into each side of the chamber for supporting and propelling the food products 1. A traditional conveyor belt assembly with its corresponding rollers and belts are excluded, there eliminating additional surfaces which a capable of collecting dirt and accidentally spilled food products.

Figure 14:
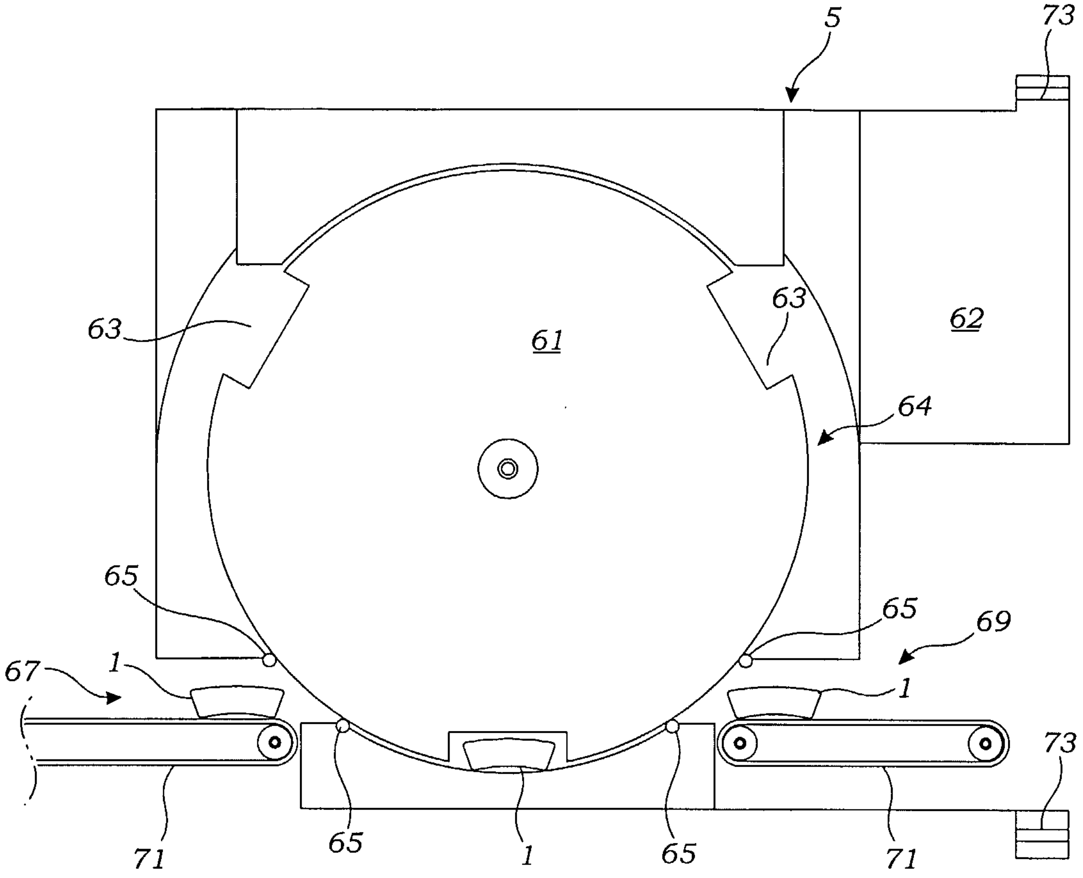
FIG. 14 is a side view illustrating a preferred continuous feed check valve for use with the conditioning tunnel of the present invention.

Each stage A1, A2, A3 and A4 is separated from the adjacent one by means of a check valve 5. In a preferred embodiment shown in FIG. 14, the check valve 5 is constructed as individual segment that can be installed and removed adjacent to other conditioning segments, such as the microwave stage and/or the cooling stage. The check valve 5 also provides for a substantially air-tight continuous linear feed for the introduction of products 1 into, at least, the heating stage. To this end, the check valve 5 includes a housing 62 having an inlet 67, a central chamber 64, and an outlet 69. For affixing the check valve to adjacent conditioning stages, the valve preferably includes a flange 73 constructed to sealingly mate to the entrance or exit of the heating or cooling stages. The check valve further includes a rotating drum 61, positioned within the housing's interior chamber 64. The drum 61 includes one or more recesses 63 sized for receipt of products 1 which are communicated to and from the check valve inlet 67 and outlet 69 by a conveyor 71. Preferably, the check valve further includes a plurality of seals 65 for effecting a substantially gaseous seal between the housing 62 and the drum 61. In operation, the conveyor 71 moves products 1 to the check valve 5, wherein the products are received within the drum's recesses 63. Continuous rotation of the drum propels the products into the next conditioning stage through outlet 69.

In an alternative embodiment shown in FIGS. 1-10, the check valve 5 essentially comprises an almost flat gate 50 with dimensions slightly greater than opening 12, made in the corresponding diving wall that separates heating stage A1, A2, A3 and A4 from the adjacent one. On the perimeter from the occluded side, the gate 50 is provided with a fitting that is mounted around opening 12, so as to guarantee effective sealing. On the other side, the gate 50 has a support bracket 52 that is linked on the top to a gear 53 engaged by a rack 54 that is moved along the vertical axis by a cylinder 55. In this case, the movement of the rack 54 is functional only to permit raising of the oscillating gate 50, whereas to carry out closure, the difference in pressure existing between the two connected stages A1 and A2, A2 and A3, A3 and A4 will cause the gate to be released and fall freely to block opening 12. In this case, it is therefore comprehensible how the pressure generated downline along conditioning tunnel A, affected by stages A1, A2, A3, will always be greater than that generated in the upline stage. With addition of the cooling stage A4 of the packaged dishes 1, where a pressure essentially less than that present in the stage immediately upline A3, the provision of stabilization stage A3 with two valves 5 is required (see FIG. 1), which open and close in opposite directions to each other. In different fashion, the valves 5 present in stages A1 and A2 have a single direction of opening, which is essentially facing downline.

With reference to FIGS. 1-10, to permit heating of the packaged dishes 1, at least A2 includes lower side 13 or the upper side 14 openings 130, 140, within which magnetrons are housed. Each magnetron, in the present case, is covered with a non-stick protective sheath, constructed of Teflon or similar material. Owing to the particular conformation of the cross-section of each stage A1, A2, A3, it is possible to provide many magnetrons, distributed in aligned rows within each stage. In a preferred embodiment, the first two stages A1 and A2 include three rows of eight magnetrons for a total of 24 magnetrons in each chamber. As shown in the drawings, stages A3 and A4 do not include magnetrons.

In a preferred embodiment of the invention, the magnetrons are cooled by water and generate 2000 W at a frequency of about 2,450 Mhz. In an alternative preferred embodiment, dual sets of magnetrons are provided in which a first set of magnetrons produces electromagnetic energy at greater than about 2000 Mhz and a second set of magnetrons produce electromagnetic energy at less than about 1000 Mhz. Even more preferably, the magnetrons produce electromagnetic energy at distinct frequency bands at approximately 915 Mhz and 2450 Mhz.

Preferably the magnetrons produce a magnetic field impulsively, in a non-constant manner, to avoid burning of products on the edges. Also, a protective shield preferably covers the magnetrons to protect against liquids and other bits of product dirtying and interfering with the magnetron's operation. The shield, made of Teflon or similar substance, may create small reduction of the microwave field. However, such reductions are considered insubstantial.

Because the energy absorption is related to the angle of incidence of the microwave radiation, it is preferable to make the angle of incidence be as close to 90° as possible. This is currently attempted by mounting the waveguide normal to the product. However, since the output of the waveguide is a spherical wave-front, the angle of incidence is only normal immediately over the waveguide. Using a dielectric type lens will take the spherical radiation pattern from the magnetron/waveguide and make it into a planar radiation pattern. This planar pattern will be normal to the product over the entire radiation pattern. Using a planar radiation pattern reduces the angle of reflection of the food surface, and increases the primary absorption, as well as maximizes the absorption depth. The portal cover of the waveguide, being a dielectric such as Teflon, can be made into the lens shape to accomplish this enhancement and increase the overall efficiency of the irradiation chamber.

The conditioning tunnel of the present invention may include magnetrons that produce an electromagnetic field which can be moved longitudinally or laterally with respect to the axis of the tunnel. To this end, the magnetrons may be connected to gimbals, tracks or other mechanical apparatus for physically moving or rotating the magnetrons relative to the tunnel to produce electromagnetic fields that can be controllably moved or rotated to alter the electromagnetic fields encountered by individual food products. Different mechanical apparatus for moving or rotating the magnetrons can be determined by those skilled in the art. Alternatively, the magnetrons may be constructed to passively move the electromagnetic field within conditioning tunnel, without physically moving the magnetrons. Constructions for passively moving the magnetic field can also be determined by those skilled in the art without undue experimentation.

Each food conditioning stage is also provided with a control system for controlling temperature and for controlling the internal pressure in the chamber for balancing the corresponding pressure present within the individual packaged dishes 1. It is known that during temperature treatments, the containers have a tendency to dilate to formation of steam. The presence of a controlled pressure within the stages has the purpose of avoiding bursting of the containers and dispersal of the liquids inside of the conditioning tunnel.

Preferably, the conditioning tunnel of the present invention includes one or more temperature sensors for sensing the temperature of the products transported through stages A1-4. The temperature sensors may be any type as can be determined by those skilled in the art. For example, traditional temperature sensors positioned adjacent to the path of the food products may be employed. However, infrared thermal cameras or sensors which measure, or pictorially display, the temperature of all containers within a stage are believed preferable. Also, preferably the infrared thermometers operate at a wavelength of approximately 1.8 μm and communicate sensor data using fiber optics to reduce the disruption generated by the substantial electromagnetic field within the chambers 11. Typically, the measured temperature is the surface temperature of the container storing the food product. However, the exterior temperature of the container provides an accurate estimate for the temperature of the product within the container.

After the initial temperature stabilization, it is important to measure the resultant temperature and uniformity of the product before entering into the microwave irradiation chamber. This can be accomplished using linear temperature sensors (imaging cameras, pyrometers or other means) and passing the product under the sensor, or by using a 2-D photo-pyrometer imaging camera which samples the entire product batch. The minimum and maximum temperatures of the products are evaluated to ensure the product temperatures are within the permissible range of the recipe. It is important that the temperature readings be representative of the food product temperature and not of the packaging temperature. For this reason, if a convection oven is used for temperature stabilization, sufficient time should be given for the packaging material to cool so the measurement will reflect the food product temperature. If a hot-plate or hot-bath conduction means is used, the top-side of the packaging material should reflect the internal product temperature without additional delay.

The measured product temperatures may be used for a number of process related adjustments. First, alarms may be activated if the product temperature is outside the allowable range of the recipe. Further thermal processing or process adjustments may be required based on these alarms. Second, the temperatures may feed-back into the initial thermal stabilization oven to manage power and or soak time to tighten the process parameters and save energy. Finally, the temperatures may feed-forward into the microwave irradiation chamber control process to increase or decrease microwave exposure to compensate for temperatures. Similar temperature detection and alarming should take place at the output of the bottom-side cycle and the top-side cycle in the irradiation chamber. By doing this one can actively monitor temperatures and exposure times to ensure proper sterilization. Additional feed-back and feed-forward process adjustments can be made based on these measurements to optimize process flow and energy usage. By managing the temperature and mass uniformity of the processed product, one is able to more tightly control the peak temperature and exposure temperature for the product, ensuring elimination of the cold-spot as well as retaining organoleptic qualities of the product. Preferably, during the transportation of the containers 1 through the tunnel, the temperature sensors continuously read the temperature of the containers, carrying out measurements on each container.

In still an additional preferred embodiment, the conditioning tunnel includes a temperature sensors which provide two dimensional temperature maps of a plurality of surfaces of products passing through the conditioning tunnel. Typically, two or more temperature sensors, which are preferably laser pyrometers or thermal cameras, are located within the conditioning tunnel so as to provide temperature gradient maps of a plurality of surfaces, such as the top and bottom, of products within the conditioning tunnel's interior chamber. The resulting two dimensional temperature maps are processed by a central processor to provide an estimated three dimensional temperature model of products which, as described below, is used to alter the conditioning properties. Using thermal data collected from the two dimensional photo-pyrometer cameras, linear pyrometers and other temperature measurement devices, a real time data model of the product can be generated. These surface temperature readings can be related to each other in a real time three dimensional model of the product by factoring in the physical dimensions of the product package, thermal transfer properties of the product, relative surface temperatures and test/audit data from the process to refine and verify the real time data model.

The tunnel of the present invention produces a density profile of each container and compares the profile parameters to reference values to ensure that each product is properly conditioned. To this end, the conditioning tunnel may include a scanning nuclear densitometer to measure product density, ideally during or immediately after the initial thermal stabilization phase as outlined above, a profile of the product density of the batch is created and that data accompanies the batch through each of the microwave irradiation chambers.

The standard processing and above criteria are good for homogeneous products, or products whose particle sizes are relatively small and thin. Products that are heterogeneous or have large pieces are susceptible to non-uniform heating. Sterilizing these products require longer heat exposures for longer periods of time to ensure proper heat conduction and cold-spot elimination. While the current processing moves the food product linearly, and/or back-and-forth, during microwave irradiation, that is not adequate for a heterogeneous food product.

To overcome the drawback, if a product is determined to have been heated insufficiently, or too greatly, preferably the system alters the heating parameters to properly condition the food products. In addition, in response to the density profile, the magnetron/waveguide may be directed toward the previously mapped dense features for adding additional energy (resulting in additional heat). Recipe-specific thermal processing can be managed and adapted for both the high-density and low-density components. Moreover, the conditioning tunnel may obtain a real-time temperature profile of the product to detect cold spots. The magnetron/waveguide may be directed toward the mapped cold spots for adding additional energy (resulting in additional heat).

The present invention provides for additional energy to be added locally within the product container to specific areas. The overall temperature profile of the product in the tray is determined using a photo-pyrometer camera or equivalent means to get a 2-dimensional thermal profile of the entire batch combined to specific temperature sensors array for the temperature distribution within the single container. In this way, cold spots can be located. To provide for localized energy within the product container, the magnetrons and waveguides may be adjusted physically or passively to provide electromagnetic energy at angles other than the optimal 90°. Altering the angle of the magnetron/waveguide allows the microwave energy to be primarily directed toward specific points in the irradiation chamber. By directing the energy, certain areas can be heated more than others. Since roughly 50% of the energy is absorbed on the first incidence at the product (with the rest being reflected), that area will heat faster than the remaining areas. By controlling the direction and timing of the primary radiation, and using the photo-pyrometer or similar means as feedback, certain areas of the product can be heated differently than others. This means that heterogeneous foods can still be sterilized without prolonging the processing time, or causing burning around the edges of the product within the container.

In a preferred embodiment of the invention, the magnetrons are controllable to produce electromagnetic fields that can controlled in both intensity and movement. If a product is determined to have been heated insufficiently, or too greatly, the magnetrons may be adjusted to alter the heating parameters to properly condition the food products. For example, where food products within the electromagnetic field of the magnetrons are found to have been heated less than expected, power to the magnetrons is increased to provide additional heating. Conversely, where the food products are determined to have been heated greater than expected, the power to the magnetrons is decreased to reduce heating to the food products.

Preferably, the conditioning tunnel is fully automated, including one or more control processors for controlling the chambers' pressure, conveyor, check valve doors, magnetrons and cooling system. The control processor is also preferably connected to the temperature sensors so that temperature measurements can be used by the control processor for determining operation of the magnetrons and conveyor. For example, preferably the conveyor is adjustable to move products forward and rearward within the conditioning tunnel. Based upon temperature measurements, the control processor causes the conveyor to move products forward or rearward into, or out from, respective magnetic fields generated by the magnetrons to provide even and thorough heating of the products. Similarly, the control processor may cause the magnetrons to increase, decrease, or move the magnetic field depending on temperature measurements of the food products. For example, temperature measurements indicating that particular food products have reached desired temperatures may cause the controller to decrease the magnetic field encountered by the food product: 1) by decreasing the power to the associated magnetron; 2) by moving the food product away from the relevant magnetic field by causing the conveyor to move the food product forwardly or rearwardly, or 3) by causing the magnetic field to move relative to the food product by physically moving the relevant magnetron or causing the relevant magnetron to passively move magnetic field relative to the food product. Conversely, temperature measurements indicating that a food product has not achieved a desired temperature may cause the control processor to: 1) increase the power to the associated magnetron; 2) move the food product into the relevant magnetic field by causing the conveyor to move the food product forwardly or rearwardly, or 3) cause the relevant magnetic field to move relative to the food product by physically moving the relevant magnetron or causing the relevant magnetron, or magnetrons, to passively move the magnetic field relative to the food product. While temperature of products are adjusted, the chamber pressure should be monitored and adjusted according to product parameters.

With reference to examples illustrated in FIGS. 13, 15 and 16, in operation the product is prepared and dosed in the prep area according to the engineered recipe. Water is added in accordance to reach the specific weight if needed. The prepared containers are transported by conveyor from the prep area to the seal packing machine where each individual package is vacuumed of oxygen, injected with nitrogen and hermetically sealed by a microwave transparent foil. The hermetically sealed packages are automatically vibrated and weighed to verify conformity to the specified values established by the recipe. The packages are automatically transferred to a baking pan which moves on a conveyor from the prep area to the sterilization chamber and finishing process.

A thermal camera and sensors array takes a temperature measurement of the surface of the packages. The measurements may be averaged, providing an indication of the average temperature data. Temperature measurements are taken for package characterization and if the measured value is not within the established tolerances, the package(s) is (are) rejected. If not rejected, the baking pan is ready to enter the sterilization chamber.

The sterilization chamber may have a quadrilateral shape or have a circular shape to better control and utilize the reflected electromagnetic power, while it is in contra-pressure. A thermal camera is placed at the entrance to map the temperature distribution on the trays. The tray is positioned inside the chamber above and below a temperature sensor array which records instantaneously the distribution of temperature inside each single container. The control processor then compares it with the one established by the recipe control. Two magnetron arrays are accommodated on the top and on the bottom of the chamber, linearly controlled and gimbalized to be able to focus the irradiation pattern over 360° with either a wide or narrow beam. Any number of magnetrons are used to generate the required sterilization temperature as established by the recipe log. These magnetrons are linearly controlled to better maintain an average power usage, and preferably, they are activated back and forth, or from bottom to top, or they can be mechanized to rotate from top to bottom, top to sides and bottom to top in a sequence governed by the control process software.

If the temperature sensors detect a temperature gradient greater than what is allowed by the recipe in any of the trays, an alarm is generated which activates the gimbalized units which focus a modulated narrow beam with high power (microburst) towards the area identified to be out of spec. Alternatively, narrow beam high power energy is focused passively from a magnetron array. Uniform temperature distribution and possible "cold spots" isolation and removal is achieved in real time providing the perfect sterilization of the product without altering any of the organoleptic properties of the product and reducing as well the duty cycle time of the process. At the end of the sterilization process, the chamber pressure is reduced to match the pressure of the cooling chamber and the trays are moved to the next phase for rapid cooling When all the trays have entered the cooling chamber, through the use of cryogenic process or cold air flow or cold water cycling, the temperature of the trays is reduced as fast as possible from the sterilization temperature to the ambient temperature. Preferably, the cooling process proceeds rapidly to better guarantee full conservation of the prepared meal organoleptic properties. After the cooling period, the trays are conveyed to the pick-up area where the single products are marked and piled up for immediate storage at regular ambient temperature, pressure and humidity.

All above phase of the process are governed by a dedicated software which is resident in the control room computer system. Preferably, each phase and function is displayed on the operator console allowing the operator to continuously monitor each single phase of the process and enabling him to take all the necessary steps to correct malfunctions and/or out of spec. values and/or parameters.

Although particular preferred embodiments of the present invention have been described herein, it is to be understood that variations may be made in the construction, materials, shape and use of the conditioning tunnel system without departing from the spirit and scope of the invention. For example only, it is preferred that the conditioning tunnel of the present invention be constructed of a modular design, in which the check valve, initial temperature stabilization, microwave sterilization and cooling stages consist of uniform generic structural segments that can be easily removed, replaced or added to provide for a wide variety of conditioning options. This allows for revised, repaired or specialized segments to be introduced into the system with minimal production down time.

Having identified the presently preferred best modes of practicing the invention, we claim:

1. A mechanized conditioning system for sterilizing products comprising:

a product conditioning unit including of a tunnel having one or more sidewalls, an entrance and an exit, said tunnel subdivided into a plurality of consecutively aligned stages including at least a heating stage and a cooling stage;

a pressurizing means for controlling the pressure of at least said heating stage;

a heating means for providing heating in said heating stage, said heating means including an inlet and an outlet, and one or more magnetrons for creating a microwave field for heating products;

a pressure sealing check valve having an inlet and an outlet, said pressure check valve further having a rotating drum having a substantially gaseous tight seal with said check valve inlet and outlet to provide a pressure seal upline or downline of at least said heating stage, said rotary drum having one or more recesses for receiving products from said check valve inlet and for discharging products through said check valve outlet for permitting the substantially continuous and linear introduction and discharge of products into or from said heating stage; and a conveyor for transporting products from upline to downline through said conditioning unit.

2. A mechanized conditioning system of claim 1 wherein said rotating drum rotates about a horizontal axis.

* * * * *